(12) United States Patent
Owaki et al.

(10) Patent No.: US 11,948,403 B2
(45) Date of Patent: Apr. 2, 2024

(54) BIOMETRIC INFORMATION AUTHENTICATION DEVICE

(71) Applicants: KABUSHIKI KAISHA TOKAI RIKA DENKI SEISAKUSHO, Aichi (JP); TOYOTA JIDOSHA KABUSHIKI KAISHA, Aichi-ken (JP)

(72) Inventors: Rijin Owaki, Aichi (JP); Yosuke Ohashi, Aichi (JP); Yuya Goto, Aichi-ken (JP); Yasuhisa Ohta, Aichi-ken (JP); Naoyuki Takada, Aichi-ken (JP); Daisuke Ogawa, Aichi (JP)

(73) Assignees: KABUSHIKI KAISHA TOKAI RIKA DENKI SEISAKUSHO, Aichi (JP); TOYOTA JIDOSHA KABUSHIKI KAISHA, Aichi-ken (JP)

( * ) Notice: Subject to any disclaimer, the term of this patent is extended or adjusted under 35 U.S.C. 154(b) by 597 days.

(21) Appl. No.: 17/266,500

(22) PCT Filed: Aug. 6, 2019

(86) PCT No.: PCT/JP2019/030992
§ 371 (c)(1),
(2) Date: Feb. 5, 2021

(87) PCT Pub. No.: WO2020/032065
PCT Pub. Date: Feb. 13, 2020

(65) Prior Publication Data
US 2021/0303893 A1    Sep. 30, 2021

(30) Foreign Application Priority Data

Aug. 7, 2018 (JP) .................... 2018-148186

(51) Int. Cl.
*G06V 40/50* (2022.01)
*B60R 25/25* (2013.01)
*G06F 21/32* (2013.01)

(52) U.S. Cl.
CPC .............. *G06V 40/50* (2022.01); *B60R 25/25* (2013.01); *G06F 21/32* (2013.01)

(58) Field of Classification Search
None
See application file for complete search history.

(56) References Cited

U.S. PATENT DOCUMENTS 6,100,811 A * 8/2000 Hsu ..................... B60R 25/2081
340/426.36
6,271,745 B1 * 8/2001 Anzai ..................... G07C 9/37
340/5.23
(Continued)

FOREIGN PATENT DOCUMENTS

EP         0976897 A1    2/2000
JP       2004-190380 A    7/2004
(Continued)

*Primary Examiner* — Syed A Roni
(74) *Attorney, Agent, or Firm* — Studebaker & Brackett PC (57) ABSTRACT

A biometric information authentication device includes a control unit, wherein, when a first biometric authentication is successfully completed based on biometric information acquired from an operator and registered biometric information preliminarily registered by a registered person and an operation for registering new registered biological information is subsequently performed, the control unit permits registration upon a successful second biometric authentication based on biometric information acquired again and the registered biometric information preliminarily registered by the registered person.

11 Claims, 4 Drawing Sheets

(56) References Cited

U.S. PATENT DOCUMENTS

| | | | | |
|---|---|---|---|---|
| 6,810,480 | B1 * | 10/2004 | Parker | G06F 21/32 |
| | | | | 713/168 |
| 6,868,170 | B1 * | 3/2005 | Fuku | B60R 25/252 |
| | | | | 340/5.53 |
| 7,141,889 | B2 | 11/2006 | Takezaki et al. | |
| 7,185,198 | B2 | 2/2007 | Nakamura et al. | |
| 9,298,996 | B2 | 3/2016 | Nada et al. | |
| 2005/0185828 | A1 | 8/2005 | Semba et al. | |
| 2006/0082437 | A1 | 4/2006 | Yuhara | |

FOREIGN PATENT DOCUMENTS

| | | | |
|---|---|---|---|
| JP | 2004-287606 A | 10/2004 | |
| JP | 2007-257099 A | 10/2007 | |
| JP | 2008-174095 A | 7/2008 | |
| JP | 2009-134422 A | 6/2009 | |
| JP | 2017-071317 A | 4/2017 | |
| JP | 2018-010470 A | 1/2018 | |

* cited by examiner

BIOMETRIC INFORMATION AUTHENTICATION DEVICE

CROSS-REFERENCE TO RELATED APPLICATIONS

The present application is a U.S. National Phase of PCT/JP2019/030992 filed on Aug. 6, 2019 claiming priority to Japanese Patent Application No. 2018-148186 filed on Aug. 7, 2018. The disclosure of the PCT Application is hereby incorporated by reference into the present application.

The present invention relates to a biometric information authentication device.

BACKGROUND ART

A start control device is known which is provided with a start switch giving an instruction to start or stop a drive source, a start-up means for starting the drive source, a fingerprint sensor for reading fingerprints, and a control means which, based on inputs from the fingerprint sensor and the start switch, implements a start-up process to control activation of the start-up means (see. e.g., Patent Literature 1).

When the start switch gives an instruction to start, the control means of the start control device performs fingerprint verification by comparing a fingerprint read by the fingerprint sensor with a pre-registered fingerprint before start-up by the start-up means, and once a match is found, the control mems authenticates the user as a genuine user and allows the start-up means to start up.

CITATION LIST

Patent Literature

Patent Literature 1: JP 2008/174095 A

SUMMARY OF INVENTION

Technical Problem

The start control device disclosed in Patent Literature 1 permits registration of a fingerprint or deletion of the registered fingerprint without going through fingerprint verification again after, e.g., a match is fond as a result of fingerprint verification. Therefore, there is a possibility that a third party who is not a registered person registers a fingerprint or deletes the registered fingerprint.

It is an object of the invention to provide a biometric information authentication device that can suppress unauthorized operations by third parties who are not registered persons.

Solution to Problem

According to a embodiment of the invention, a biometric information authentication device comprises a control unit, wherein, when a first biometric authentication is successfully completed based on biometric information acquired from an operator and registered biometric information preliminarily registered by a registered person and an operation for registering new registered biological information is subsequently performed, the control unit permits registration upon a successful second biometric authentication based on biometric information acquired again and the registered biometric information preliminarily registered by the registered person.

According to a embodiment of the invention, it is possible to provide a biometric information authentication device that can suppress unauthorized operations by third parties who are not registered persons.

DESCRIPTION OF EMBODIMENTS

Summary of the Embodiment

A biometric information authentication device in a embodiment has a control unit. When a first biometric authentication is successfully completed based on biometric information acquired from a operator and registered biometric information preliminarily registered by a registered person and an operation for registering new registered biological information is subsequently performed, the control unit permits registration upon a successful second biometric authentication based on biometric information acquired again and the registered biometric information preliminarily registered by the registered person.

In case of registration of new registered biometric information, this biometric information authentication device does not permit registration without successful second biometric authentication even if the first biometric authentication is successfully completed. Therefore, unlike when such a configuration is not adopted, attempt of the second biometric authentication by a third party who is not a registered person will not be successful and it is thus possible to suppress unauthorized operations by the third party.

Embodiment (General Configuration of a Start Switch Device 1)

Figure 1A:
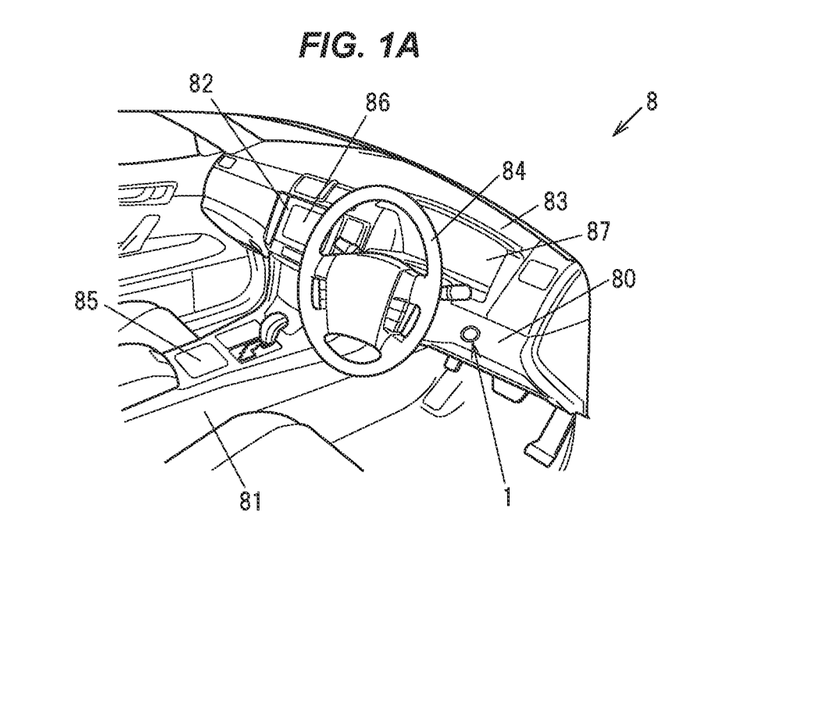
FIG. 1A is explanatory diagram illustrating the inside of a vehicle in which a start switch device in an embodiment is arranged.
Figure 1B:
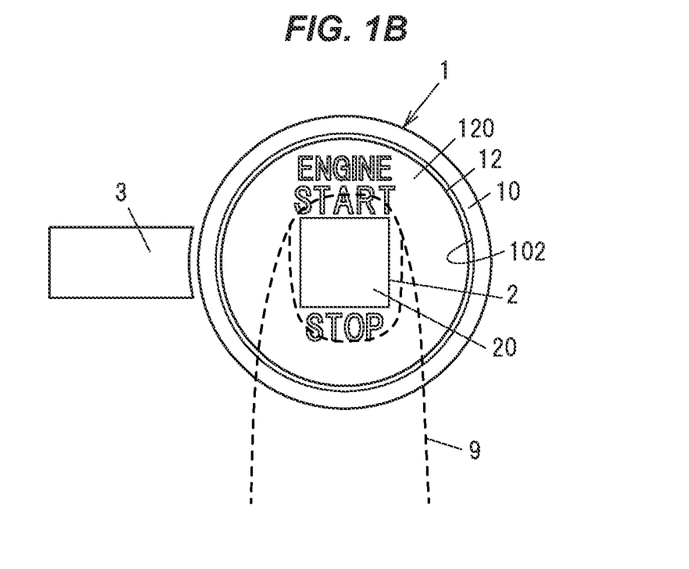
FIG. 1B is a front view showing the start switch device in the embodiment.
Figure 2A:
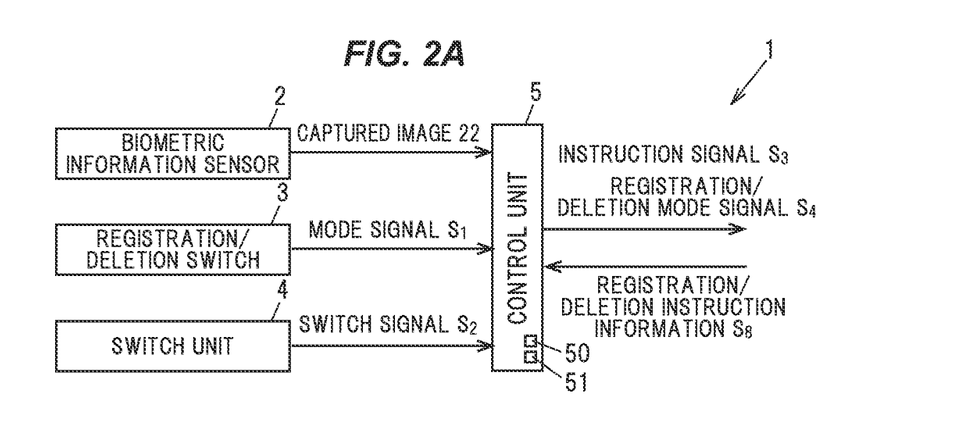
FIG. 2A is a block diagram illustrating the start switch device in the embodiment.
Figure 2B:
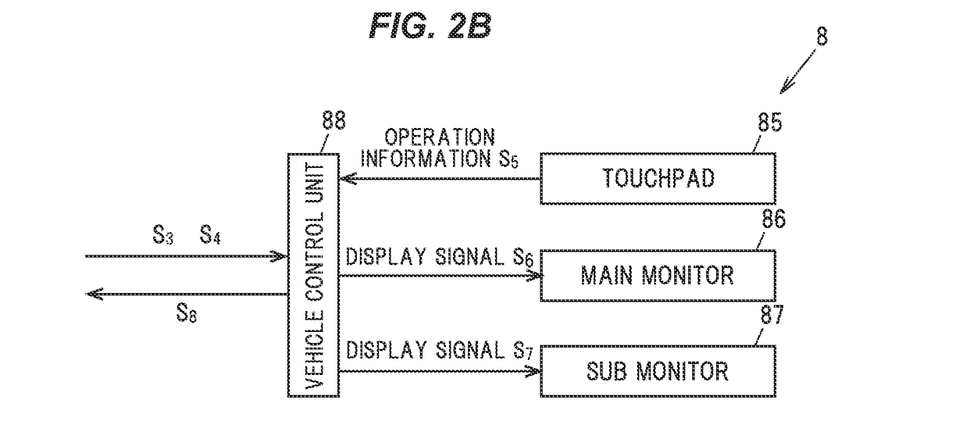
FIG. 2B is a block diagram illustrating the vehicle.
Figure 2C:
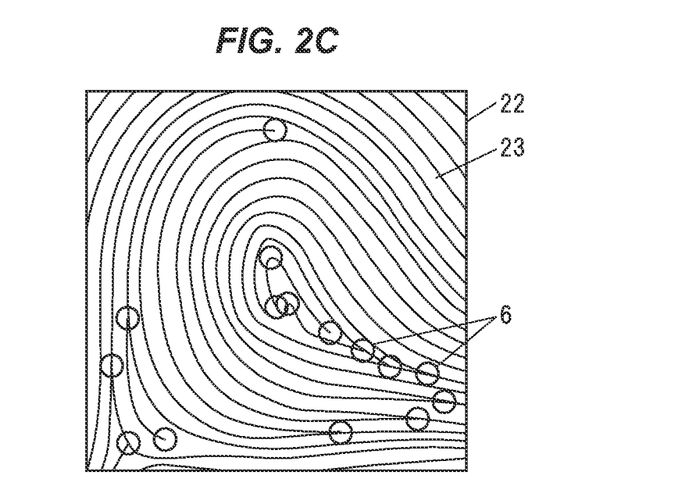
FIG. 2C is an explanatory diagram illustrating a captured image that is captured by a biometric information sensor of the start switch device in the embodiment.
Figure 3A:
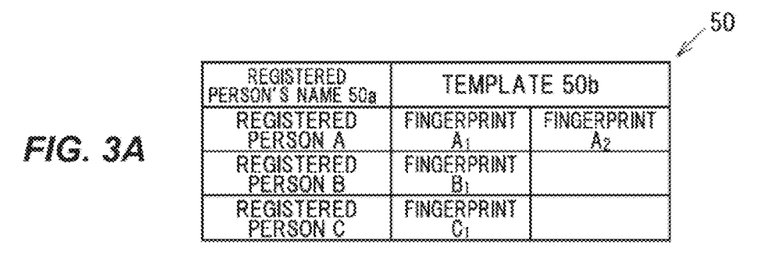
FIG. 3A is an explanatory diagram illustrating registered biometric information held on the start switch device in the embodiment.
Figure 3B:
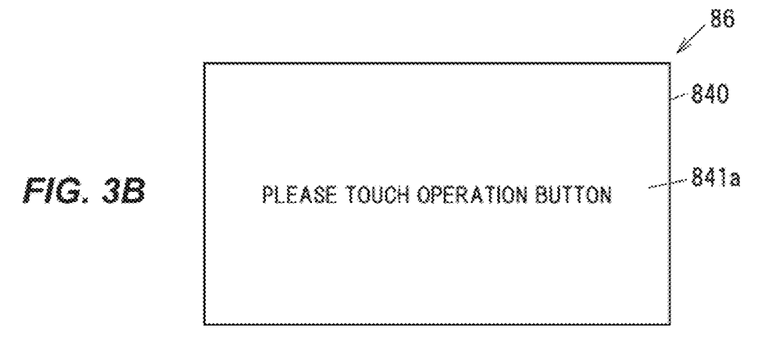
FIG. 3B is a explanatory diagram illustrating an image to encourage to try biometric information reading again when the stat switch device in the embodiment is in a registration mode or a deletion mode.
Figure 3C:
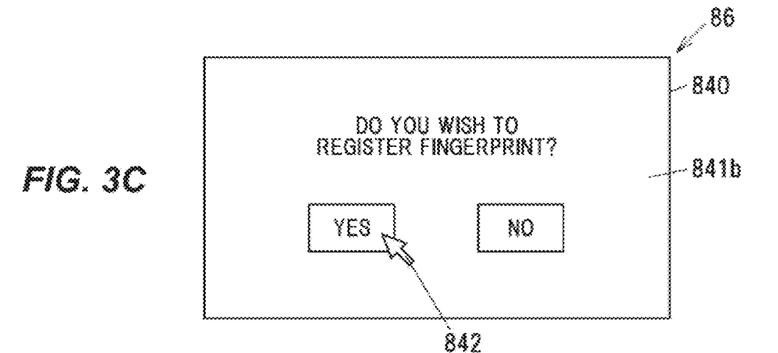
FIG. 3C is an explanatory diagram illustrating a display image that is displayed when the start switch device in the embodiment is in the registration mode.
Figure 3D:
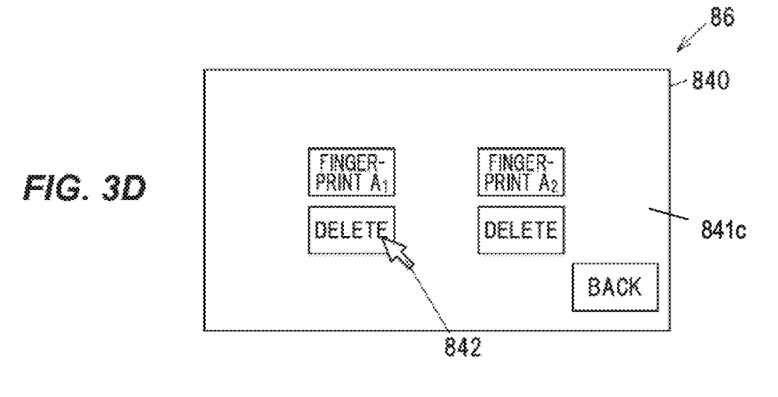
FIG. 3D is an explanatory diagram illustrating a display image that is displayed when the start switch device in the embodiment is in the deletion mode.

FIG. 1A is an explanatory diagram illustrating the inside of a vehicle in which a start switch device in the embodiment is arranged, and FIG. 1B is a front view showing the start switch device in the embodiment. FIG. 2A is an example of a block diagram illustrating the start switch device in the embodiment, FIG. 2B is an example of a block diagram illustrating the vehicle, and FIG. 2C is an explanatory diagram illustrating a captured image that is captured by a biometric information sensor of the start switch device in the embodiment. FIG. 3A is an explanatory diagram illustrating registered biometric information held on the start switch device in the embodiment. FIG. 3B is an explanatory diagram illustrating an image to encourage to try biometric information reading again when the start switch device in the embodiment is in a registration mode or a deletion mode, FIG. 3C is a schematic diagram illustrating a display image that is displayed when the start switch device in the embodiment is in the registration mode, and FIG. 3D is an explanatory diagram illustrating a display image that is displayed when the start switch device in the embodiment is in the deletion mode.

In each drawing of the embodiment described below, a scale ratio may be different from an actual ratio. In addition, in FIGS. 2A and 2B, flows of main signals and information, etc., are indicated by arrows.

As shown in FIG. 1A, the start switch device 1 as the biometric information authentication device is arranged on, e.g., a panel 80 located in front of a operator sitting in a driver's seat and at the periphery of a steering wheel 84, a floor console 81 located between the driver's seat and the front passenger seat, or the steering wheel 84, etc. This start switch device 1 can instruct a vehicle control unit 88 of a vehicle 8 to start, or to prepare to start, a drive system of the vehicle 8 by a push operation (ON operation), and instruct to stop the drive system by a next push operation (OFF operation).

Start-up of the drive system of the vehicle 8 and the power state transition of the vehicle 8 are judged by, e.g., the vehicle control unit 88 based on an instruction signal $S_3$ output from the start switch device 1 and the operating conditions for a shifting device, etc.

In particular, when the drive system is an internal combustion engine (e engine), the engine is started by a push operation performed in a state in which the operating conditions for the shifting device or a braking device are met. Meanwhile, when the drive system is a motor, preparation for start, which is a current supply to the motor, is carried out by a push operation performed in a state in which the above-described operating conditions are met. Furthermore, when the drive system is an engine/motor hybrid, start or preparation for start corresponding to the drive system prioritized at the time of start is carried out by a push operation performed in a state in which the above-described operating conditions we met. An OFF operation performed after this ON operation gives an instruction to stop the drive system.

Then, when a push operation is performed without activation of the brake device which is the operating condition, the start switch device 1 outputs the instruction signal $S_3$ to perform transition of power state such as between OFF (power of), ACC (allowing some of electronic devices to be used) or ON (allowing all electronic devices to be used), as an example. Based on, e.g., such an instruction signal $S_3$ and the above-mentioned operating condition, the vehicle control unit 88 controls the power source. In this regard, the biometric information authentication device is not limited to the start switch device 1 and may be used for, e.g., authentication for locking or unlocking doors or authentication for logging in to electronic devices, etc.

As shown in FIG. 2A, the start switch device 1 has. e.g., a control unit 5. When a first biometric authentication is successfully completed based on biometric information 23 acquired from an operator and registered biometric information 50 preliminarily registered by a registered person and an operation for registering new registered biological information 50 is subsequently performed, the control unit 5 permits registration upon a successful second biometric authentication based on biometric information 23 acquired again and the registered biometric information 50 preliminarily registered by the registered person.

As shown in FIG. 1B, this start switch device 1 is provided with, e.g., a cylindrical min body 10 and an operation button 12. The operation button 12 is inserted into an opening 102 of the main body 10. In addition, the start switch device 1 is also provided with, e.g., a biometric information sensor 2, a registration/deletion switch 3 and a switch unit 4, as shown in FIG. 2A.

The control unit 5 is configured to permit deletion upon a successful second biometric authentication when an operation for deleting the registered biometric information 50 preliminarily registered by the registered person is performed after the first biometric authentication is successfully completed.

The control unit 5 is also configured to not permit registration or deletion when the second biometric authentication is unsuccessful.

The registration or deletion of the registered biometric information 50 is performed during a period in which validity of the first biometric authentication continues. The period in which validity of the first biometric authentication continues is, e.g., a period from when the first biometric authentication is successfully completed to when a power source of the vehicle 8 is turned off.

Meanwhile, as an example, the vehicle 8 has a touchpad 85, a main monitor 86, a sub monitor 87 and the vehicle control unit 88, as shown in FIG. 2B.

The touchpad 85 is arranged on, e.g., the floor console 81, as shown in FIG. 1A. The touchpad 85 is, e.g., a capacitive touchpad and outputs operation information $S_5$ to the vehicle control unit 88 based on an operation performed thereon.

As an example, the main monitor 86 is arranged on a center console 82 as shown in FIG. 1A, bit it is not limited thereto. The main monitor 86 is, e.g., a liquid crystal monitor and carries out display based on a display signal Se output from the vehicle control unit 88.

As an example, the sub monitor 87 is arranged on a instrument panel 83 in front of the driver's seat, as shown in FIG. 1A. The sub monitor 87 is, e.g., a liquid crystal monitor and carries out display based on a display signal $S_7$ output from the vehicle control unit 88. The position for arranging the sub monitor 87 is not limited to, e.g., the instrument panel 83 and may be another position such as a head-up display, etc.

In the following description, a message image related to registration or deletion of the registered biometric information 50 is displayed on the main monitor 86. However, it is not limited thereto. The message image may be displayed on the sub monitor 87 or may be displayed on the main monitor 86 and the sub monitor 87.

The vehicle control unit 88 is, e.g., a microcomputer composed of a CPU (Central Processing Unit), and a RAM (Random Access Memory) and a ROM (Read Only Memory) as semiconductor memories, etc. The vehicle control unit 88 is electromagnetically connected to the start switch device 1 via, e.g., an in-vehicle LAN (Local Area Network) such as CAN (Controller Area Network) or LIN (Local Interconnect Network).

(Configuration of the Biometric Information Sensor 2)

The biometric information sensor 2 is arranged so that, e.g., a reading surface 20 is exposed on an operation surface 120 of the operation button 12, as shown in FIG. 1B.

The biometric information sensor 2 is configured to read, e.g., a fingerprint of an operating finger 9 as the biometric information 23, as shown in FIGS. 1B and 2C. However, the biometric information 23 is not limited to the fingerprint of the operating finger 9 and may be a vein of the operating finger 9, a vein of a palm, an iris of an eye, or a shape of a portion of the body such as face. In addition, the biometric information sensor 2 does not need to be mounted on the start switch device 1 as long as it can read the biometric information 23 such as, e.g., iris even if located at a distance from an object to be operated.

In case of reading, e.g., a fingerprint, the biometric information sensor 2 used here is a sensor of optical, capacitive, electric field strength measuring, pressure-sensitive, or thermal type, etc., which is configured to read a fingerprint.

Meanwhile, in case of reading. e.g., a vein of the operating finger 9 or of a palm, the biometric information sensor 2 used is a sensor configured to read a vein based on reflection of emitted infrared radiation.

Then, in case of reading, e.g., both a fingerprint and a vein, the biometric information sensor 2 used is a sensor configured to extract a fingerprint ad a vein by processing an image captured under visible light.

Furthermore, in case of reading, e.g., an iris, the biometric information sensor 2 used is a sensor configured to read an iris by processing an image captured under infrared light emission.

Still further, in case of reading, e.g., a shape of a portion of the body such as face, the biometric information sensor 2 used is a sensor configured to read an uneven shape on a subject based on depths at plural measurement points on the captured subject.

The biometric information sensor 2 in the present embodiment is a capacitive sensor that reads a fingerprint, as example. This biometric information sensor 2 is configured to read the biometric information 23 from the operation finger 9 which is in contact with the reading surface 20 when the operator performs a push operation on the operation button 12. Alternatively, the reading surface 20 may be arranged under the operation surface 120 without being exposed on the operation surface 120.

The biometric information sensor 2 is provided with, e.g., plural detection electrodes which are arranged in rows and columns in a grid patter under the reading surface 20. As an example, several ten thousand to several hundred thousand detection electrodes are formed and arranged at intervals of several μm to several tens μm.

The biometric information sensor 2 is configured to scan all detection electrodes by, e.g., repeating a process of reading capacitances of the detection electrodes arranged in one row while changing columns and then subsequently reading capacitances of the detection electrodes arranged in a different row. The scanning cycle is about 100 ms, a an example.

The biometric information sensor 2 outputs, e.g., a captured image 22, which is formed based on plural capacitances read by scanning, to the control unit 5. The captured image 22 is formed based on. e.g., capacitances in one cycle.

In particular, the biometric information sensor 2 generates the captured image 22 by, e.g., classifying the capacitances into capacitances of not less than a predetermined threshold value to be assigned "1" and capacitances of less than the threshold value to be assigned "0" and associating the capacitances with the positions of the detection electrodes.

The captured image 22 shown in FIG. 2C is produced in such a manner that the positions of the detection electrodes assigned "1" described above are shown in black and the positions of the detection electrodes assigned "0" are shown in wiite, as an example. The circles in the drawing are added to show some of characteristic features 6 (described later).

The high-capacitance positions are positions of ridges of the fingerprint which are close to the detection electrodes, hence, capacitance is high. Meanwhile, the low-capacitance positions are positions of valleys of the fingerprint which are far from the detection electrodes, hence, capacitance is low. Therefore, as example, the captured image 22 shown in FIG. 2C is obtained when the high-capacitance positions are shown in black and the low-capacitance positions are shown in white. The image shown in black in the captured image 22 is the read biometric information 23.

The control unit 5 may be configured to, e.g., select a captured image 22, which is suitable for extraction of the characteristic features 6, from plural captured images 22 captured after the contact of the operating finger 9 with the reading surface 20, or may be configured to use the captured image 22, which is captured by being triggered by the event that the switch unit 4 is turned on, for extraction of the characteristic features 6.

(Configuration of the Registration/Deletion Switch 3)

As an example, the registration/deletion switch 3 is arranged adjacent to the main body 10, as shown in FIG. RB. The registration/deletion switch 3 may be, e.g., a physical switch or a capacitive touch switch. The registration/deletion switch 3 in the present embodiment is configured as a touch switch.

After, e.g., authentication by a mobile device such as electronic key and the first biometric authentication are successfully completed, a registered person can select a registration mode or a deletion mode for the registered biometric information 50 by performing a tap operation or a double tap operation on the registration/deletion switch 3.

The registration mode is a mode allowing for a new registration of the registered biometric information 50. It is possible to switch to the registration mode by performing, e.g., a tap operation on the registration/deletion switch 3.

The deletion mode is a mode allowing for deletion of the registered biometric information 50 that is already registered. It is possible to switch to the deletion mode by performing, e.g., a double tap operation on the registration/deletion switch 3. In this regard, when, e.g., the registration/deletion switch 3 is not operated, the start switch device 1 is in an authentication mode.

The registration/deletion switch 3 outputs a mode signal $S_1$, which corresponds to the tap or double tap operation performed thereon, to the control unit 5. The control unit 5 determines, e.g., whether the mode is the registration mode or the deletion mode based on the mode signal $S_1$, generates a registration/deletion mode signal $S_4$ corresponding to the determined mode, and outputs it to the vehicle control unit 88.

(Configuration of the Switch Unit 4)

As a example, the switch unit 4 is configured as a rubber dome switch which comes into contact with a end portion of the operation button 12 on the opposite side to the operation surface 120. The rubber dome switch is provided with, e.g., a rubber dome which generates an elastic force and has a movable contact, and a switch substrate on which the rubber dome is arranged and which has a fixed contact facing the movable contact.

When the operation button 12 is pushed into the main body 10 by a push operation, the movable contact is electrically conducted to the fixed contact due to deformation of the rubber dome and a switch signal $S_2$, which indicates that the switch is turned on, is output to the control unit 5. The start switch device 1 is configured that when, e.g., the push operation ends, the operation button 12 returns to the initial position by an elastic force of the rubber dome.

(Configuration of the Control Unit 5)

The control unit 5 is, e.g., a microcomputer composed of a CPU performing calculation and processing, etc., of the acquired data according to a stored program, and a RAM and a ROM as semiconductor memories, etc. The ROM stores, e.g., a program for operation of the control unit 5. The RAM is used as, e.g., a storage area for storing the registered biometric information 50, a similarity threshold value 51 and calculation results, etc. In addition, the control unit 5 has, inside thereof, a means for generating a clock signal, and operates based on the clock signal.

The registered biometric information 50 is, e.g., information associating a registered person's name 50a with a template 50b of each registered person, as shown in FIG. 3A. The registered person's name may be associated with, e.g., an electronic key or mobile device, and may be input by operating an input device such as the touchpad 85. However, it is not limited thereto.

In the registered biometric information 50 shown in FIG. 3A, the biometric information 23 (fingerprints) of registered persons A to C are registered, as an example. The registered person A has registered, e.g., a fingerprint A1 and a fingerprint A2 as the template 50b. The fingerprint A1 made the fingerprint A2 are, e.g., the templates 50b of different fingers of the registered person A. Meanwhile, the registered person B has registered, e.g., a fingerprint B1 as the template 5b. Furthermore, the registered person C has registered, e.g., a fingerprint C1 as the template 50b.

Registering the registered biometric information 50 means that, e.g., the registered person B newly registers a fingerprint B2 as the template 50b. Meanwhile, deleting the registered biometric information 50 means that, e.g., the registered person A deletes the already registered fingerprint A2.

This template 50b is used for authentication of the biometric information 23 and is composed of mainly the characteristic features 6. Next, the characteristic feature 6 will be described.

The control unit 5 performs, e.g., an extraction process on the captured image 22 and extracts the characteristic features 6. The extraction process is, e.g., a process of extracting fingerprint ridges, etc.

The characteristic feature 6 is, e.g., a center point, a bifurcation point, ma ending point or a delta, etc., as shown in FIG. 2C, but it is not limited thereto. The center point is a point at the center of the fingerprint. The bifurcation point is a point at which a fingerprint ridge bifurcates. The ending point is a point at which a ridge ends. The delta is a point at which ridges from three directions meet.

The control unit 5 extracts, e.g., the characteristic features 6 from the captured image 22. The control unit 5 then compares, e.g., the acquired registered biometric information 50 to the biometric information 23 from which the characteristic features 6e extracted, and calculates a degree of similarity based on the positions of the characteristic features 6 and distances between the characteristic features 6, etc. Then, when the switch unit 4 is ON and the degree of similarity is not less than the similarity threshold value $S_1$, the control unit 5 outputs the instruction signal $S_3$ upon determination that the biometric information 23 is successfully authenticated.

The similarity threshold value 51 is 80%, as an example. In other words, when, e.g., the number of the characteristic features 6 of the biometric information 23 used for authentication is eighty and when not less than sixty-four characteristic features 6 match those of the registered biometric information 50, the control unit 5 determines that the operator is a registered person. The match here includes match of the position of the characteristic feature 6 and a distance between the characteristic features 6, etc.

In the meantime, the vehicle control unit 88 may be configured to implement, e.g., based on the acquired instruction signal $S_3$, settings of on-vehicle devices which have been set by the registered person who successfully completed the first biometric authentication. The on-vehicle device when being. e.g., a seat driving device moves a seat to a seat position which has been set by the registered person. Meanwhile, the on-vehicle device when being, e.g., an air conditioner implements the settings, such as the set temperature and the air volume, which have been set by the registered person. Furthermore, the on-vehicle device when being, e.g., a mirror driving device drives mirrors to the positions which have been set by the registered person. Electromagnetic connection is. e.g., connection using at least one of connection via a conductor, connection via light which is a kind of electromagnetic wave, and connection via radio waves which is also a kind of electromagnetic wave.

The control unit 5 controls the biometric information sensor 2 so that the switch signal $S_2$ output from the switch unit 4 triggers scanning of the reading surface 20, as a example. In this case, since a push operation is being performed on the operation surface 120, a contact area between the operating finger 9 and the reading surface 20 is larger than that when touching the reading surface 20 before the push operation, and more characteristic features 6 can be extracted.

(Registration and Deletion of the Registered Biometric Information 50)

When an operation for newly registering or deleting the registered biometric information 50 is performed during the period in which validity given by successful completion of the first biometric authentication continues, the control unit 5 permits registration or deletion upon successful completion of the second biometric authentication based on the biometric information 23 acquired again and the registered biometric information 50 that is preliminarily registered.

Registration

When, e.g., the mode signal $S_1$ is input from the registration/deletion switch 3, the control unit 5 determines whether the mode is registration or deletion, and outputs the registration/deletion mode signal $S_4$ to the vehicle control unit 88. When determined that, e.g., the mode is registration based on the input registration/deletion mode signal SU, the vehicle control unit 88 causes a message image 841a to be displayed on a display screen 840 of the main monitor 86 to make the operator proceed to the second biometric authentication, as shown in FIG. 3B.

As an example, this message image 841a is composed of a message "Please touch the operation button", etc., as shown in FIG. 3B to encourage to touch the reading surface 20 with the operating finger 9 again.

After the biometric information 23 of the operating finger 9 is read again, the control unit 5 performs the second biometric authentication. Then, when the second biometric authentication is successful, the control unit 5 outputs the instruction signal $S_3$, which indicates that the second biometric authentication is successful, to the vehicle control unit 88.

The vehicle control unit 88 causes, e.g., a message image 841b to be displayed on the display screen 840 of the main monitor 86 based on the input instruction signal $S_3$ to confirm the intention of registration, as shown in FIG. 3C.

As an example, the message image 841b is composed of a message containing "Do you wish to register a fingerprint?", "Yes" and "No", etc., as shown in FIG. 3C. The operator uses. e.g., the touchpad 85 to move a cursor 842 displayed on the display screen 840, selects "Yes" or "No" in the image, and confirm it by a push operation or a double tap operation, etc.

When "Yes" is selected and confirmed, the vehicle control unit 88 outputs registration/deletion instruction information $S_8$, which indicates that "Yes" is selected and confirmed, to the control unit 5. Based on this registration/deletion instruction information $S_8$, the control unit 5 generates a template 50b using the characteristic features 6, etc., extracted based on the captured image 22 that is captured through the reading surface 20 after acquisition of the registration/deletion instruction information $S_8$, and registers the template 50b. This template 50b is registered as a new template of the registered persons name 50a in the registered biometric information 50 used for the second biometric authentication.

Meanwhile, when "No" is selected and confirmed, the vehicle control unit 88 outputs the registration/deletion instruction information $S_4$, which indicates that "No" is selected and confirmed, to the control unit 5. Based on this registration/deletion instruction information $S_8$, the control unit 5 switches from the registration mode to the authentication mode.

Deletion

When. e.g., the mode signal $S_1$ is input from the registration/deletion switch 3, the control unit 5 determines whether the mode is registration or deletion, and outputs the registration/deletion mode signal $S_4$ to the vehicle control unit 88. When determined that, e.g., the mode is deletion based on the input registration/deletion mode signal $S_4$, the vehicle control nit 88 causes the message image 841a to be displayed on the display screen 840 of the main monitor 86 to make the operator proceed to the second biometric authentication, as shown in FIG. 3B.

After the biometric information 23 of the operating finger 9 is read again, the control unit 5 performs the second biometric authentication. Then, when the second biometric authentication is successful, the control unit 5 outputs the instruction signal $S_3$, which indicates that the second biometric authentication is successful, to the vehicle control unit 88.

The vehicle control unit 88 causes. e.g., a message image 841c to be displayed on the display screen 840 of the main monitor 86 based on the input instruction signal $S_3$ to allow for selection of the fingerprint to be deleted ad confirm the intention of deletion, as shown in FIG. 3D.

As an example, when determined that the operator is the registered person A based on the result of the second biometric authentication, the message image 841c is composed of a message containing "Fingerprint A1", "Fingerprint A2", "Delete" and "Back", etc., as shown in FIGS. 3A and 3D. The operator uses, e.g., the touchpad 85 to move the cursor 842 displayed on the display screen 840, selects "Deletion" or "Back" in the image, and confirm it by a push operation or a double tap operation, etc.

The message image 841c displayed at the time of deletion is generated based on, e.g., the registered biometric information 50 stored in the control unit 5. Therefore, the control unit 5 may be configured to, e.g., output information used to generate message image 841c, or may be configured to share the registered biometric information 50 with the vehicle control unit 88.

When "Delete" is selected and confirmed, the vehicle control unit 88 outputs the registration/deletion instruction information $S_8$, which indicates the fingerprint selected and confirmed for "Deletion", to the control unit 5. Based on this registration/deletion instruction information $S_8$, the control unit 5 deletes the template 50b selected and confirmed.

Meanwhile, when "No" is selected and confirmed, the vehicle control wait 88 outputs registration/deletion instruction information $S_8$, which indicates that "No" is selected and confirmed, to the control wait 5. Based on this registration/deletion instruction information $S_8$, the control unit 5 switches from the deletion mode to the authentication mode.

Meanwhile, as a modification, the templates 50b we associated with the registrable number of switches, such a the registration/deletion switch 3, and registered or deleted by the switches, a an example. In this case, the control unit 5 performs, e.g., registration or deletion of the template 50b associated with the operated switch without displaying the message image 841b and the message image 841c shown in FIGS. 3C and 3D.

The registration and deletion described above ca be carried out as long as both authentications are successful even if the registered person attempting the first biometric authentication is different from the registered person attempting the second biometric authentication. As a modification, the control unit 5 is configured to perform biometric authentication in such a manner that the registered biometric information 50 of the same registered person is used in the first biometric authentication and the second biometric authentication. In this modification, registration or deletion of the registered biometric information 50 is performed only by the registered person who successfully completed the first biometric authentication.

Meanwhile, as another modification, the control unit 5 is configured to perform the second biometric authentication with higher authentication accuracy than the first biometric authentication. In this modification, when, e.g., the similarity threshold value 51 used in the first biometric authentication is 80%, the similarity threshold value 1 used in the second biometric authentication is changed to be higher than 80%, such as 85% or 90%.

In biometric authentication, the false acceptance rate increases (high convenience) when the false reaction rate is set to low, and the false rejection rate increases (high security) when the false acceptance rate is set to low. As such, the false rejection rate and the false acceptance rate, i.e., convenience and security are in a trade-off relation and it is not possible to reduce the false acceptance rate down to zero. Therefore, if a person who has not registered his/her fingerprint repeats biometric authentication attempts many times, this person may be successfully authenticated.

Since the second biometric authentication is more difficult than the first biometric authentication in this modification, it is possible to suppress unauthorized operations such as registration or deletion by third parties, as compared when using the same similarity threshold value.

As still another modification, the control unit 5 is configured to limit the number of attempts of the second biometric authentication. This number is five times, as an example. The control unit 5 counts the number of unsuccessful authentication attempts and does not permit registration or deletion of the registered biometric information 50 when the number becomes not less than five times. Since the number of attempts of the second biometric authentication is limited in this modification, the possibility of successful authentication caused by repeating biometric authentication attempts can be reduced as compared when the number is not limited.

Figure 4:
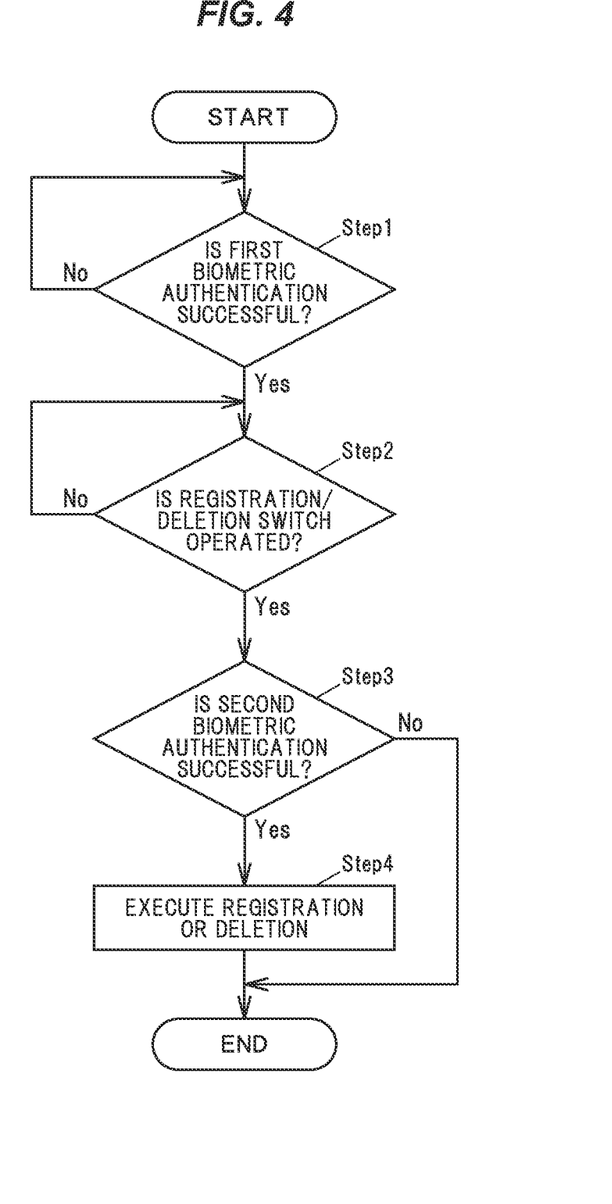
FIG. 4 is a explanatory diagram illustrating an operation of the start switch device in the embodiment.

Next, an example of an operation of the start switch device 1 in the present embodiment will be described along with the flowchart of FIG. 4.

(Operation)

When it is "Yes" in Step 1, i.e., when the first biometric authentication is successfully completed based on the biometric information 23 read during a push operation performed on the operation button 12 and the registered biometric information 50 (Step 1: Yes), the control unit 5 of the start switch device 1 outputs the instruction signal $S_3$, which indicates that the first biometric authentication is successful, to the vehicle control unit 88. The vehicle control unit 88 starts, e.g., the drive system based on this instruction signal $S_3$.

Next when it is "Yes" in Step 2, i.e., when it is determined based on the mode signal $S_1$ that the registration/deletion switch 3 is operated (Step 2: Yes), the control unit 5 generates the registration/deletion mode signal $S_4$ corresponding to the selected mode and outputs it to the vehicle control unit 88. Based on the acquired registration/deletion mode signal $S_4$, the vehicle control unit 88 causes, e.g., the message image 841a shown in FIG. 3B to be displayed.

Next, the control unit 5 performs the second biometric authentication based on the biometric information 23, which is read when the operator touches the operation surface 120 of the operation button 12, and the registered biometric information 50. When the second biometric authentication is successful (Step 3: Yes), the control unit 5 outputs the instruction signal $S_3$, which indicates that registration or deletion is permitted, to the vehicle control unit 88.

In response to the acquired instruction signal $S_3$, the vehicle control unit 88 causes the main monitor 86 to display a message image based on the selected mode. Then, the vehicle control unit 88 generates the registration/deletion instruction information Sa based on the selection made through the touchpad 85 and output it to the control unit 5.

Next, the control unit 5 performs registration or deletion of the registered biometric information 50 based on the acquired registration/deletion instruction information $S_8$ (Step 4) and ends registration or deletion of the registered biometric information 50.

Meanwhile, when the second biometric authentication is not successful in Step 3 (Step 3: No), the control unit 5 ends the process without permitting registration or deletion of the registered biometric information 50.

Here, if a push operation for instructing to stop the drive system or to transition the power state of the vehicle 8 is performed during when monitoring an operation on the registration/deletion switch 3 in Step 2, the control unit 5 ends registration or deletion of the registered biometric information 50.

Effects of the Embodiment

The start switch device 1 in the present embodiment can suppress unauthorized operations by third parties who are not registered persons. In particular, in case of registration of new registered biometric information 50 or deletion, the start switch device 1 does not permits registration or deletion without successful second biometric authentication even if the first biometric authentication is successfully completed. Therefore, unlike when such a configuration is not adopted, attempt of the second biometric authentication by a third party who is not a registered person will not be successful and it is thus possible to suppress unauthorized operations by the third party.

Since the start switch device 1 uses the registered biometric information 50 of the same registered person in the first biometric authentication as well as the second biometric authentication, registration or deletion of the registered biometric information 50 is performed only by the registered person who successfully completed the first biometric authentication, unlike when such a configuration is not adopted.

With the start switch device 1, it is not possible to register or delete the registered biometric information 50 only by successfully completing the first biometric authentication. Therefore, even if the registered person who successfully completed the first biometric authentication is away from the vehicle, it is possible to suppress unauthorized operations by a third party, such as registration of the biometric information 23 of this third party or deletion of the registered biometric information 50 that is already registered, unlike when registration or deletion can be carried out upon successful completion of the first biometric authentication.

Alternatively, as another embodiment, a program may be provided to implement a biometric information authentication method in which, when a first biometric authentication is successfully completed based on biometric information acquired from an operator and registered biometric information preliminarily registered by a registered person and an operation for registering new registered biological information is subsequently performed, registration is permitted upon a successful second biometric authentication based on biometric information acquired again and the registered biometric information preliminarily registered by the registered person, or a computer-readable storage medium storing such a program may be provided.

Although some embodiments ad modifications of the invention have been described, these embodiments and modifications are merely examples and the invention according to claims is not to be limited thereto. These new embodiments ad modifications may be implemented in various other forms, and various omissions, substitutions and changes, etc., can be made without departing from the gist of the invention. In addition, all combinations of the features described in these embodiments and modifications are not necessary to solve the problem of the invention. Further, these embodiments and modifications we included within the scope and gist of the invention ad also within the invention described in the claims and the range of equivalency.

REFERENCE SIGNS LIST

1 START SWITCH DEVICE
2 BIOMETRIC INFORMATION SENSOR
3 REGISTRATION/DELETION SWITCH
5 CONTROL UNIT
23 BIOMETRIC INFORMATION
50 REGISTERED BIOMETRIC INFORMATION
841a-841c MESSAGE IMAGE

The invention claimed is:

1. A biometric information authentication device, comprising
a biometric information sensor, and
a control unit, wherein,
when a first biometric authentication is successfully completed based on biometric information acquired by the biometric information sensor from an operator and registered biometric information preliminarily registered by a registered person and an operation for registering new registered biological information is subsequently performed, the control unit permits registration upon a successful second biometric authentication based on biometric information acquired by the same biometric information sensor again and the registered biometric information preliminarily registered by the registered person wherein the first and second biometric authentications are both performed on the same biometric information sensor located on an operation button that operates a start switch of a vehicle.

2. The biometric information authentication device according to claim 1, wherein, when an operation for deleting the registered biometric information preliminarily registered by the registered person is performed after the first biometric authentication is successfully completed, the control unit permits deletion upon the successful second biometric authentication.

3. The biometric information authentication device according to claim 1, wherein the control unit does not permit registration or deletion when the second biometric authentication is unsuccessful.

4. The biometric information authentication device according to claim 1, wherein the control unit performs biometric authentication in such a manner that the registered biometric information of the same registered person is used in the first biometric authentication and the second biometric authentication.

5. The biometric information authentication device according to claim 1, wherein the control unit performs the second biometric authentication with higher authentication accuracy than the first biometric authentication.

6. The biometric information authentication device according to claim 1, wherein the control unit limits a number of attempts of the second biometric authentication during a period in which validity given by successful completion of the first biometric authentication continues.

7. The biometric information authentication device according to claim 6, wherein the control unit outputs an instruction signal for transitioning a power state of a vehicle, and the period in which validity given by successful completion of the first biometric authentication continues is set as a period from when the first biometric authentication is successfully completed to when a power source of the vehicle is turned off.

8. The biometric information authentication device according to claim 1, wherein, when the operation for registering new registered biometric information or an operation for deleting the registered biometric information preliminarily registered by the registered person is performed, the control unit issue a notification to encourage to proceed to the second biometric authentication.

9. The biometric information authentication device according to claim 8, wherein the control unit uses display when issuing a notification to encourage to proceed to the second biometric authentication.

10. The biometric information authentication device according to claim 1, further comprising a switch on which the operation for registering new registered biometric information or an operation for deleting the registered biometric information preliminarily registered by the registered person is performed.

11. The biometric information authentication device according to claim 1, wherein the control unit allows the operation for registering new registered biological information only if it is performed within a predetermined amount of time from the successful completion of the first biometric authentication.

* * * * *